United States Patent [19]

Guzman Llansa et al.

[11] 4,352,935
[45] Oct. 5, 1982

[54] PROCESS FOR OBTAINING P-ACETAMIDO PHENOL α-METHYL-4(2'THIENYL-CARBONYL) PHENYL ACETATE

[76] Inventors: Eduardo Guzman Llansa, Calle siglo XX, No. 20; Pablo Arino Maestrojuan, Corcega, 89, both of Barcelona; Enrique Melendez Andreu, Fray-Luis Amigó, 2, Zaragoza, all of Spain

[21] Appl. No.: 323,992

[22] Filed: Nov. 23, 1981

Related U.S. Application Data

[62] Division of Ser. No. 137,442, Apr. 4, 1980, abandoned.

[30] Foreign Application Priority Data

Apr. 4, 1979 [ES] Spain .................................. 479.300

[51] Int. Cl.$^3$ ..................... C07D 333/16; A61K 31/38
[52] U.S. Cl. .......................................... 549/72; 424/275
[58] Field of Search .......................................... 549/72

[56] References Cited

U.S. PATENT DOCUMENTS

| | | | |
|---|---|---|---|
| 3,903,114 | 9/1975 | Martret et al. | 549/72 |
| 4,064,132 | 12/1977 | Janssen et al. | 549/72 |
| 4,153,718 | 5/1979 | Goudie | 549/72 |
| 4,159,986 | 7/1979 | Clemence et al. | 549/72 |

*Primary Examiner*—Alan Siegel
*Attorney, Agent, or Firm*—Wenderoth, Lind & Ponack

[57] ABSTRACT

Para-acetamidophenol α-methyl-4(2'-thienyl-carbonyl) phenyl acetate, having anti-inflammatory activity, is provided, along with a process for its preparation by reacting α-methyl-4(2'-thienyl-carbonyl) phenyl acetic acid or a reactive species thereof with p-acetamidophenol in an aprotic organic solvent and, when the reactive species is an acid halide, the reaction is carried out also in the presence of a hydrohalic binding compound.

1 Claim, No Drawings

PROCESS FOR OBTAINING P-ACETAMIDO PHENOL α-METHYL-4(2'THIENYL-CARBONYL) PHENYL ACETATE

This application is a division of Ser. No. 137,442, filed Apr. 4, 1980 now abandoned.

Since the anti-inflammatory and analgesic properties of α-methyl-4-(2'-thienyl-carbonyl)phenyl acetic acid (I) are known from published works (the bibliography in Niemegers. Arzneim. Forsch. Drug. Res. 25 (10) 1516-1519, 1975) and from tests conducted on this compound, various derivatives thereof have been prepared by the present inventors in an attempt to improve its physical and pharmacological characteristics. The tests carried out demonstrated that the derivative p-acetamidophenol α-methyl-4(2'-thienyl-carbonyl)phenyl acetate (II) possesses in turn a very interesting anti-inflammatory activity, having an $ED_{50}=4.5$ mg/Kg in the test for the anti-oedematous activity using the technique of acute oedema implantation by carrageenin induced in rats.

The object of the present invention is to obtain p-acetamidophenol α-methyl-4(2'-thienyl-carbonyl)phenyl acetate corresponding to the formula (II).

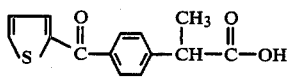

(I)

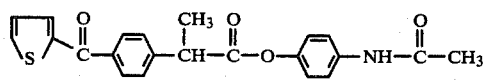

(II)

The compound of formula (II) is obtained from the acid (I) or from any one of the reactive species thereof having the formula (III), wherein X represents halogen or mixed anhydride (R—COO—, where R can be represented by straight chain alkyl, branched alkyl or straight chain alkoxy) by reaction with p-acetamidophenol (IV), in the presence of a suitable aprotic organic solvent and in the presence of a hydrohalic binding compound, when the reactive species is an acid halide.

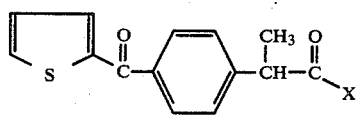

(III)

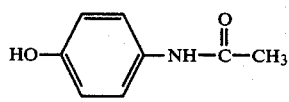

(IV)

The reaction is carried out using any of the normal techniques such as, for example, thin layer chromatography.

The end product can be isolated from the reaction mixture by any convenient procedure, such as, for example, elimination of the solvent used in the reaction, dissolution of the residue in an organic solvent, nonmiscible in water, washing the dissolved residual repeatedly with water and basic solutions to eliminate the acid impurities, eliminating the organic solvent by evaporation and recrystallizing the residue with a suitable solvent.

It is clear that various procedures can be used to carry out the object of the invention without modifying the essential characteristics thereof. The following illustrative and non-limiting examples give an idea of the practical possiblities of the described process.

EXAMPLE 1 p-Acetamidophenol α-methyl-4(2'-thienyl-carbonyl) phenyl acetate (a) 26 g (0.1 mol) of α-methyl-4(2'-thienyl-carbonyl)-phenyl acetic acid, 300 ml of dry ethyl ether, 7.8 ml (0.1 mol) of thionyl chloride and 3 drops of DMF were allowed to react for 24 hours at room temperature. The mixture was concentrated to dryness and the crude acid chloride thus obtained was used in the following step.

(b) To a solution, cooled in an ice/water bath, of 15.1 g (0.1 mol) of p-acetamidophenol and 14 ml (0.1 mol) of triethylamine in 200 ml of dry acetone, was added the acid chloride obtained in the preceding step dissolved in 50 ml of acetone. The addition took place over a period of 45 minutes. The mixture was allowed to react for 20 hours at room temperature. The acetone was eliminated in vacuo and ethyl acetate was added to the residue, which was washed repeatedly with water, 0.1 N NaOH, and water, to neutralization.

The organic extracts were dried, decolorized and concentrated to dryness. A white solid having a weight of 25.5 g was obtained. Yield 65%. It was recrystallized with 175 ml of methanol. Weight 22 g; m.p. 144°–145° C.

EXAMPLE 2 p-Acetamidophenol α-methyl-4(2'-thienyl-carbonyl)phenyl acetate

To 2.6 g (0.01 mol) of α-methyl-4(2'-thienyl-carbonyl) phenyl acetic acid dissolved in 25 cc of tetrahydrofuran were added 1.4 cc of triethylamine, and the mixture was allowed to react for 15 minutes, whereafter it was cooled to −10° C., and 0.95 cc (0.01 mol) of ethyl chloroformate in 5 cc of tetrahydrofuran were added slowly. The mixture was allowed to react at −10° C. for 45 minutes. Immediately thereafter 1.51 g (0.01 mol) of p-acetamidophenol dissolved in 15 cc of tetrahydrofuran were added slowly. After addition, the mixture was maintained at −10° C. for 30 minutes until room temperature was slowly reached and stirring was continued for 20 hours. At the end of this time the solvent was eliminated in vacuo, the residue was dissolved in ethyl acetate and was washed with water, a solution of 1 N NaOH, and water to neutralization. The ethyl acetate extract was dried, decolorized and concentrated to dryness, obtaining a solid white paste which crystallized with 10 cc of methanol. Weight 2.2 g; m.p. 143°–144° C. Yield 56%.

We claim:
1. The compound of the formula

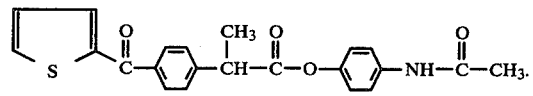

* * * * *